(12) United States Patent
Fujikake (10) Patent No.: US 10,881,535 B2
(45) Date of Patent: Jan. 5, 2021

(54) JOINT REGULATING APPARATUS

(71) Applicant: TOYOTA JIDOSHA KABUSHIKI KAISHA, Toyota (JP)

(72) Inventor: Yoshinori Fujikake, Nagakute (JP)

(73) Assignee: TOYOTA JIDOSHA KABUSHIKI KAISHA, Toyota (JP)

(*) Notice: Subject to any disclaimer, the term of this patent is extended or adjusted under 35 U.S.C. 154(b) by 260 days.

(21) Appl. No.: 15/925,839

(22) Filed: Mar. 20, 2018

(65) Prior Publication Data

US 2018/0289512 A1 Oct. 11, 2018

(30) Foreign Application Priority Data

Apr. 11, 2017 (JP) .................... 2017-078542

(51) Int. Cl.
*A61F 2/66* (2006.01)
*A61F 5/01* (2006.01)
*A61F 2/50* (2006.01)

(52) U.S. Cl.
CPC .......... *A61F 2/6607* (2013.01); *A61F 5/0127* (2013.01); *A61F 2002/5043* (2013.01); *A61F 2005/0167* (2013.01); *A61F 2005/0179* (2013.01); *A61H 2201/164* (2013.01)

(58) Field of Classification Search
CPC .... A61F 5/0127; A61F 5/0102; A61F 5/0195; A61F 2005/0132; A61H 1/00; A61H 1/02; A61H 1/0237; A61H 1/0266; A61H 2201/0173; A61H 2201/0176; A61H 2201/018; A61H 2201/12; A61H 2201/1436; A61H 2201/1445; A61H 2201/1671

USPC .............................................. 601/5
See application file for complete search history.

(56) References Cited

U.S. PATENT DOCUMENTS

| 2,477,591 A | 8/1949 | Follis | |
| 2,567,195 A * | 9/1951 | Ellery | A61F 5/0127 602/28 |
| 4,320,747 A * | 3/1982 | Daniell, Jr. | A61F 5/0123 602/16 |

(Continued)

FOREIGN PATENT DOCUMENTS

| JP | 2007-54086 | 3/2007 |
| JP | 2015-154858 | 8/2015 |

(Continued)

*Primary Examiner* — Rachel T Sippel
*Assistant Examiner* — Benjamin M. Kusiak
(74) *Attorney, Agent, or Firm* — Oblon, McClelland, Maier & Neustadt, L.L.P.

(57) ABSTRACT

A joint regulating apparatus configured to regulate a movable range of a joint connecting a first bone part of a wearer with a second bone part of the wearer, includes a first member attached to a part of a body located on a side of the first bone, a second member attached to a part of the body located on a side of the second bone, and a joint mechanism configured to support the first and second members so that the first and second members can swing with respect to each other along a movable direction of the joint in a predetermined regulated swing range, in which the joint mechanism includes an elastic mechanism configured to, when the first and second members tend to swing with respect to each other beyond the swing range, exert an elastic force against the swing.

7 Claims, 12 Drawing Sheets

(56) References Cited

U.S. PATENT DOCUMENTS

| | | | | | |
|---|---|---|---|---|---|
| 4,915,098 | A | * | 4/1990 | Young | A61F 5/0123 602/16 |
| 5,242,379 | A | * | 9/1993 | Harris | A43B 7/20 602/16 |
| 6,129,690 | A | * | 10/2000 | Hamlin | A61F 5/0125 602/16 |
| 6,155,998 | A | * | 12/2000 | Gilmour | A61F 5/0127 135/77 |
| 6,171,272 | B1 | * | 1/2001 | Akita | A61F 5/0127 602/27 |
| 8,696,764 | B2 | * | 4/2014 | Hansen | A61F 2/6607 606/16 |
| 10,610,384 | B2 | * | 4/2020 | Byars | A61F 2/66 |
| 2002/0133108 | A1 | * | 9/2002 | Jagodzinski | A61F 5/0123 602/16 |
| 2005/0215931 | A1 | * | 9/2005 | Opahle | A61F 5/0125 602/23 |
| 2008/0051686 | A1 | * | 2/2008 | Ashihara | A61F 5/0102 602/28 |
| 2010/0222727 | A1 | * | 9/2010 | Naegerl | A61F 5/0123 602/16 |
| 2012/0059296 | A1 | * | 3/2012 | Kompa | A61F 5/0123 602/16 |
| 2016/0067075 | A1 | * | 3/2016 | Malinowski | A61F 5/0113 602/28 |

FOREIGN PATENT DOCUMENTS

| | | |
|---|---|---|
| JP | 5807888 | 11/2015 |
| JP | 2017-148215 | 8/2017 |
| JP | 2017-158645 | 9/2017 |
| NL | 1020676 C2 | 11/2003 |

* cited by examiner

DORSIFLEXION ROTATION

JOINT REGULATING APPARATUS

CROSS REFERENCE TO RELATED APPLICATIONS

This application is based upon and claims the benefit of priority from Japanese patent application No. 2017-78542, filed on Apr. 11, 2017, the disclosure of which is incorporated herein in its entirety by reference.

BACKGROUND

The present disclosure relates to a joint regulating apparatus.

Assistance equipment that is attached to a leg of a user and assists walking of the user has been known. For example, in assistance equipment disclosed in Japanese Unexamined Patent Application Publication No. 2007-54086, a lower-thigh frame attached to a lower thigh of a user is rotatably connected to a sole frame on which the user places his/her sole. In this assistance equipment, assisting motions are controlled by driving a link mechanism by using a motor so that a plantar-flexion/dorsiflexion motion of an ankle joint is assisted and the plantar-flexion/dorsiflexion motion of the ankle joint does not exceed a movable range.

SUMMARY

The present inventors have found the following problem. Power-driven assistance equipment tends to have a large size and hence its usability as equipment used for a joint of a human body including an ankle joint is not satisfactory. Even in the case of passive assistance equipment that does not provide power-driven assistance to joint motions, depending on a disease state of a user, it is necessary to regulate a movable range of the assistance equipment so that the user does not excessively bend his/her joint. However, when a regulation range in which a user is allowed to bend his/her joint is made narrower than a range in which the user can physically and naturally bend the joint, a large impact is given to a regulation member at both ends of the regulated range by a bending force of the joint. When the regulation member is damaged or worn out by such impacts, it becomes impossible to accurately manage the allowable motion range and/or troublesome replacement of components is required. As a result, the usability of the assisting equipment is impaired. Further, in some cases, such damage interferes with a rehabilitation plan due to the need to repair the equipment and/or acquire a replacement component.

The present disclosure has been made to solve the above-described problem and an object thereof is to provide a joint regulating apparatus having a simple structure and high durability, and configured to regulate a movable range of a joint.

A first exemplary aspect is a joint regulating apparatus configured to regulate a movable range of a joint connecting a first bone part of a wearer with a second bone part of the wearer, including: a first member attached to a part of a body located on a side of the first bone; a second member attached to a part of the body located on a side of the second bone; and a joint mechanism configured to support the first and second members so that the first and second members can swing with respect to each other along a movable direction of the joint in a predetermined regulated swing range, in which the joint mechanism includes an elastic mechanism configured to, when the first and second members tend to swing with respect to each other beyond the swing range, exert an elastic force against the swing.

The provision of such an elastic mechanism makes it possible to release a large impact, which would otherwise be exerted on the regulation member by a bending force of the joint, and thereby to reduce damage and wear of the regulation member. By preventing damage and wear of the regulation member, it is possible to accurately manage an allowable motion range and thereby to carry out a rehabilitation plan without a hitch.

Further, the above-described joint mechanism can include: a regulation member directly or indirectly fixed to the first member, the regulation member being configured to regulate the swing range; and a swing member directly or indirectly fixed to the second member, the swing member being configured to come into contact with a regulation member at one of the ends of the swing range and at the other end of the swing range. Further, the above-described elastic mechanism can include: a displacement member configured to allow the swing member, after the swing member comes into contact with the regulation member, to further swing around a contact point by displacing a swing axis of the swing member; and an elastic member configured to exert an elastic force by resisting a displacement of the displace member. By adopting a structure for displacing the swing axis as described above, it is possible to easily insure rigidity for releasing a large impact.

Further, in this case, the elastic member is preferably configured so as to press the displacement member so that the swing axis is not displaced when the swing member swings within the swing range. By the above-described configuration, it is possible to prevent the swing axis from being displaced in the set swing range and hence to prevent a user from having an unnatural feeling during normal use.

In this case, the joint mechanism is preferably configured to include: a first-part bushing integrally formed with a holder part, the holder part being configured to support the regulation member, the first-part bushing being configured to receive a shaft surface of the swing member; and a second-part bushing integrally formed with the displacement member, the second-part bushing being configured to form a ring with the first-part bushing and thereby to receive the shaft surface. By the above-described configuration, it is possible to receive the shaft surface of the swing member by both of the bushings in the set swing range and thereby to achieve a smooth swing.

In this case, the displacement member preferably has a contact surface configured to receive a pressing force from the elastic member and thereby to come into contact with the holder part when the swing member swings in the swing range, and the second-part bushing is preferably not pressed onto the shaft surface by the elastic member. By the above-described configuration, since the elastic member does not press the shaft surface of the swing member in the set swing range, it does not interfere with the smooth swing of the swing member.

In the above-described joint regulating apparatus, the elastic member is preferably a spring and the displacement member is preferably connected to the spring though a toggle mechanism. By adopting the toggle mechanism as described above, a spring having a small external shape and a large spring constant can be used, thus enabling the elastic mechanism to absorb a large impact force even though it has a small size. Note that the spring is preferably a spring coil disposed along a circumferential direction with respect to the swing axis. By disposing the spring coil along the circumferential direction with respect to the swing axis, it is possible to reduce the necessary space even further.

The above-described joint regulating apparatus is preferably used in such a manner that one of the first and second members is a lower-thigh frame attached to a lower thigh of the wearer and the other of the first and second members is a sole frame on which the wearer places his/her sole. Further, in the joint mechanism, the swing range is preferably determined so that a range of a plantar-flexion motion and a dorsiflexion motion of an ankle joint of the wearer is regulated. In the regulation of motions of an ankle joint, large impacts tend to occur particularly at both ends of the regulation range and hence a number of effects of the above-described elastic mechanism can be enjoyed.

According to the present disclosure, it is possible to provide a joint regulating apparatus having a simple structure and high durability, and configured to regulate a movable range of a joint.

The above and other objects, features and advantages of the present invention will become more fully understood from the detailed description given hereinbelow and the accompanying drawings which are given by way of illustration only, and thus are not to be considered as limiting the present invention.

DESCRIPTION OF EMBODIMENTS

The present disclosure is explained hereinafter by using embodiments. However, the present disclosure according to the claims is not limited to the below-shown embodiments. Further, each of the components explained in the embodiments is not necessarily indispensable as means for solving the problem.

Figure 1:
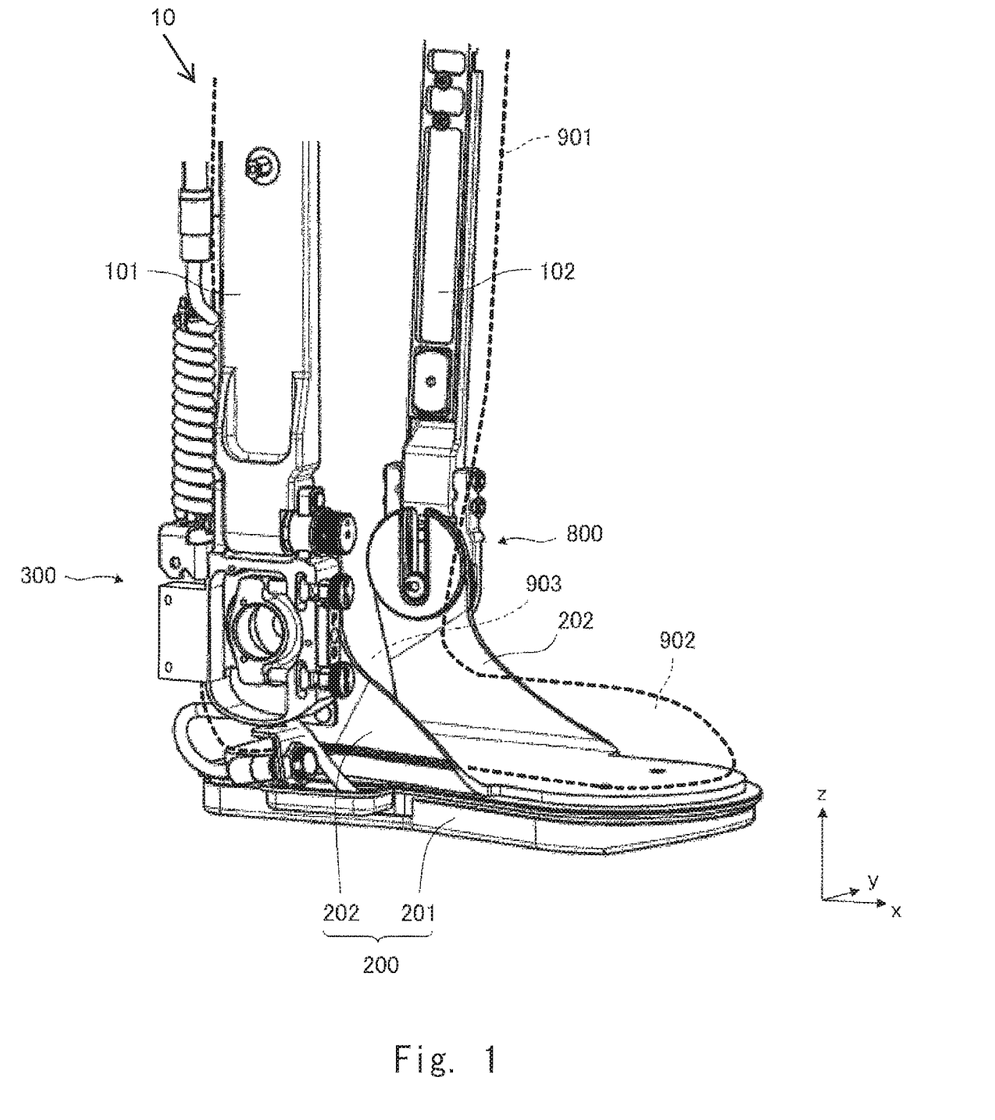
FIG. 1 is a perspective view of an external appearance of an ankle joint regulating apparatus according to an embodiment.

FIG. 1 is a perspective view of an external appearance of an ankle joint regulating apparatus 10 according to an embodiment. The ankle joint regulating apparatus 10 is a regulation apparatus that regulates a movable range of an angle joint 903 that connects a bone of a lower-thigh (i.e., a shinbone and a fibula) of a wearer with his/her anklebone. The ankle joint regulating apparatus 10 is mainly composed of lower-thigh frames 101 and 102. Lower-thigh frame 101 is located on a side of the bone of the lower-thigh and supports a lower thigh 901, a sole frame 200 that is located on a side of the anklebone and supports a part from an ankle to a tip of a foot 902, and a joint mechanism 300 that supports these two frames so that they can swing in a swing range regulated along a movable direction of the angle joint 903.

The sole frame 200 includes a bottom plate 201 having a placement surface on which the wearer places his/her sole, and side plates 202 vertically disposed on sides of the bottom plate 201. More specifically, the joint mechanism 300 connects a lower end of the lower-thigh frame 101 with the outer-side side plate 202 in such a manner that they can swing. The sole frame 200 is attached to the foot 902 thorough an attachment belt or the like (not shown). For example, when the wearer wears a shoe-like cup sole, the sole frame 200 may be constructed so as to fix the cup sole. As described later, the joint mechanism 300 has such a structure that the joint mechanism 300 swings in a range that is narrower than a range in which the angle joint 903 can be physically and naturally bent. Note that FIG. 1 shows a state in which a cover of the joint mechanism 300 is removed in order to clarify relations between components/structures shown in FIG. 1 and those shown in the subsequent drawings. In actual use, a cover is attached to the joint mechanism 300 in order to prevent dust and the like from entering into the mechanism.

The lower-thigh frame 102 is located on a side of the lower thigh 901 opposite to the side on which the lower-thigh frame 101 is located. That is, the lower-thigh frames 101 and 102 are attached so as to sandwich the lower thigh 901 therebetween and supports the lower thigh 901. Note that the lower-thigh frames 101 and 102. are attached to the lower thigh 901 through an attachment belt or the like (not shown).

The ankle joint regulating apparatus 10 includes a connecting mechanism 800 that connects the lower-thigh frame 102 with the inner-side side plate 202 in such a manner that they can swing. Unlike the joint mechanism 300, the connecting mechanism 800 does not include a structure for regulating the swing. That is, the movable range of the angle joint 903 is not regulated by the connecting mechanism 800 located on the inner side thereof, but is instead regulated by the joint mechanism 300 located on the outer side thereof. By adopting the above-described structure, it is possible to adjust the regulation range without detaching the ankle joint regulating apparatus 10 from the wearer.

Note that in FIG. 1, it is assumed that the diseased leg is the right leg and a state in which the joint mechanism 300 is disposed on the outer side of the right leg is shown. In this embodiment, the ankle joint regulating apparatus 10 is a regulation apparatus for a right leg. However, needless to say, it is possible to manufacture a regulation apparatus for a left leg in which the joint mechanism 300 is disposed on the outer side of the left leg. Further, as shown in the figures, a direction from an ankle toward a toe is defined as a positive direction on an x-axis, and a direction toward the inner side on a plane (i.e., a surface) of the bottom plate 201 is defined as a positive direction on a y-axis. Further, a direction toward an upper body along the thigh is defined as a positive direction on a z-axis. The same coordinate system as that shown in FIG. 1 is shown in each of the subsequent drawings to clarify each direction.

Figure 2:
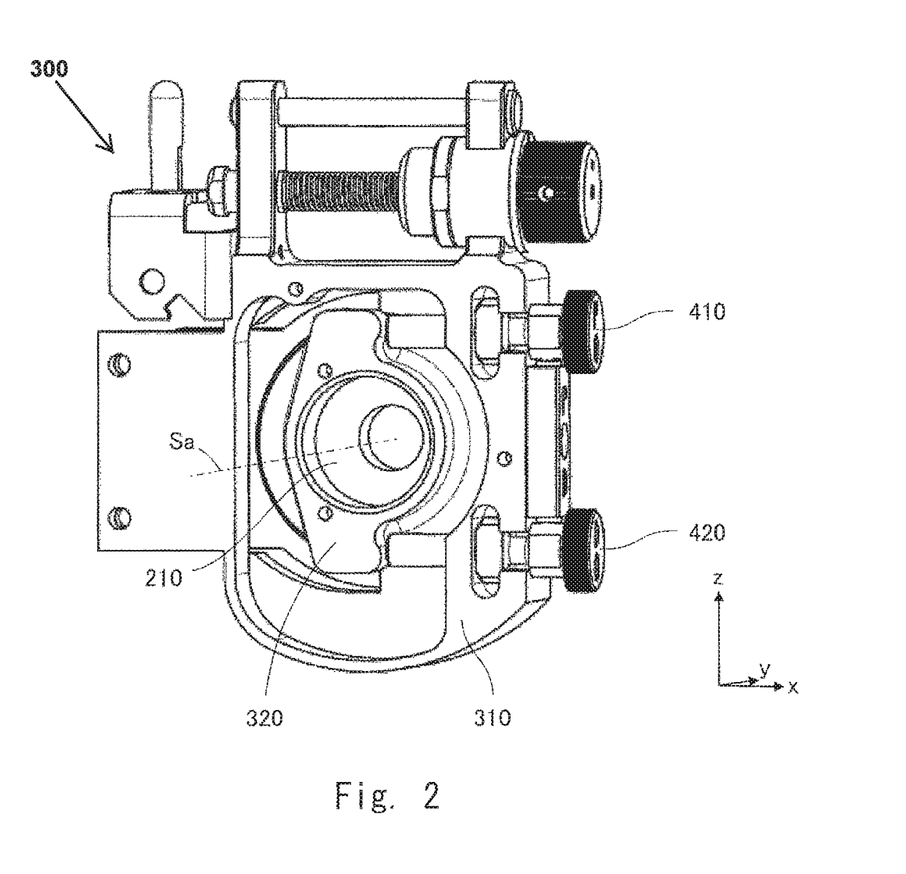
FIG. 2 is a perspective view of an external appearance of a joint mechanism.

FIG. 2 is a perspective view of an external appearance of the joint mechanism 300. Similarly to FIG. 1, FIG. 2 shows a state in which a cover is removed. The joint mechanism 300 is mainly composed of a holder 310, a swing shaft 320, and stopper pins 410 and 420.

The holder 310 is fixed to the lower-thigh frame 101. For example, the holder 310 is formed by carving it out of an aluminum block. Note that the holder 310 may be connected to the lower-thigh frame 101 so that it is enabled to slightly rotate around the x-axis with respect to the lower-thigh frame 101.

The swing shaft 320 is fixed to the side plate 202 of the sole frame 200 through a coupling member 210. The swing shaft 320 is pivotally supported on the holder 310 in such a manner that it can swing around a swing axis Sa. That is, when the wearer performs a plantar-flexion motion and a dorsiflexion motion by moving his/her leg joint, the sole frame 200 follows the motions and hence the swing shaft 320 swings around the swing axis Sa with respect to the holder 310.

The stopper pin 410 is inserted into the holder 310 from a side thereof and regulates, of the swing range of the swing shaft 320, the swing angle of the plantar-flexion motion. The stopper pin 420 is inserted into the holder 310 from the side thereof and regulates, of the swing range of the swing shaft 320, the swing angle of the dorsiflexion motion. Specific structures and specific motions are described later.

Figure 3:
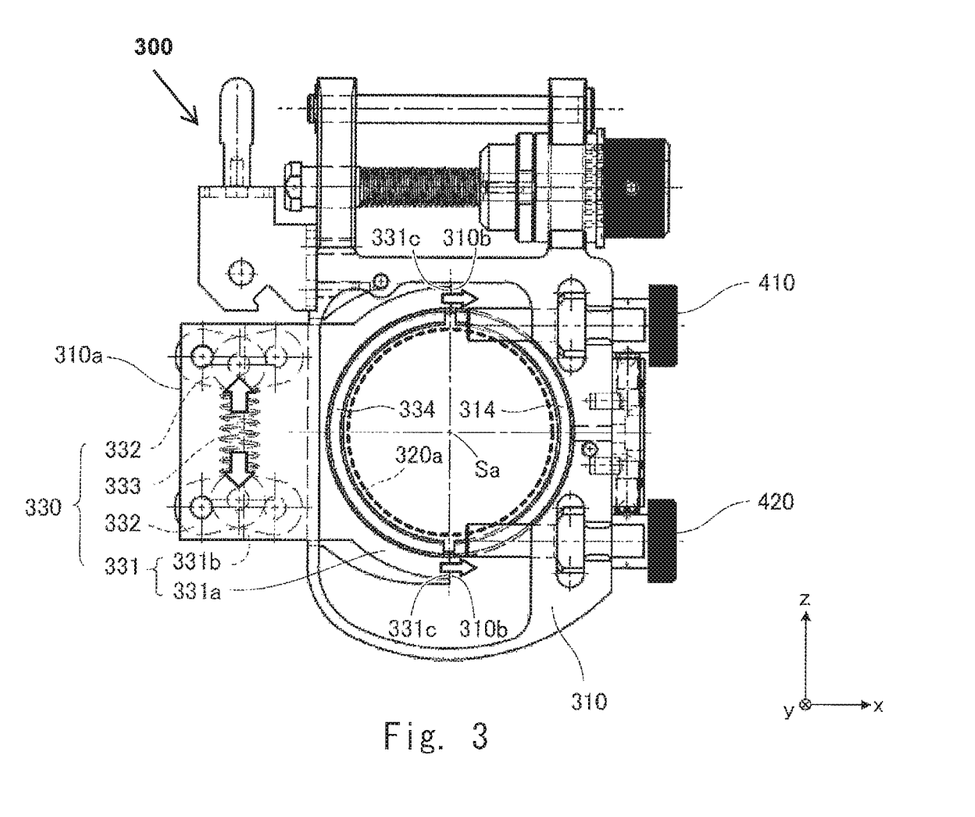
FIG. 3 is a front view showing a structure of the joint mechanism in which a swing shaft is removed.
Figure 4:
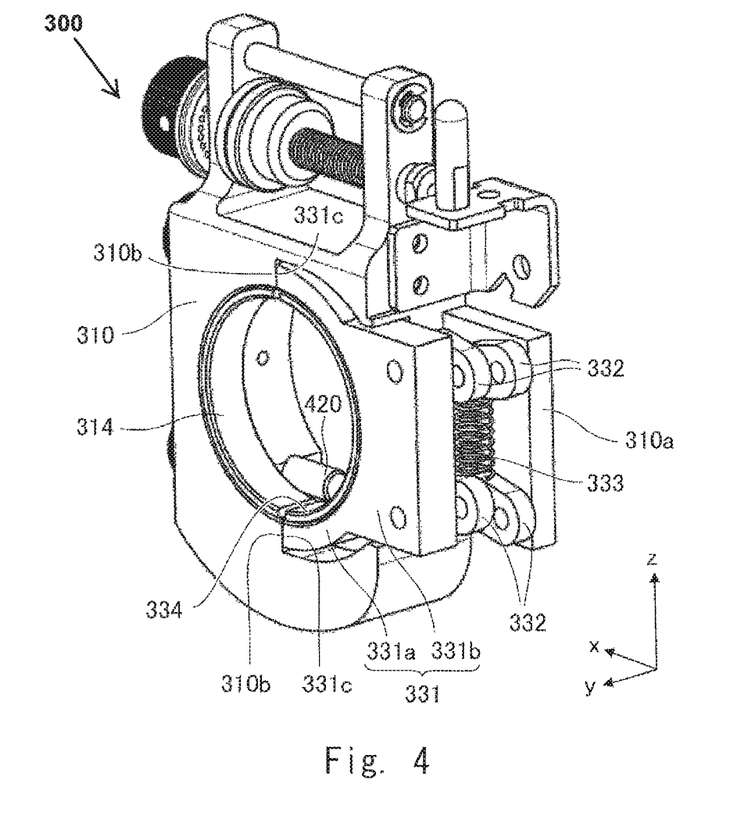
FIG. 4 is a rear-side perspective view showing a structure of the joint mechanism in which the swing shaft is removed.

FIG. 3 is a front view showing a structure of the joint mechanism 300 in which the swing shaft 320 is removed. A part of the structure that cannot be viewed from the front is indicated by dotted lines. Further, FIG. 4 is a rear-side perspective view showing a structure of the joint mechanism 300 in which the swing shaft 320 is removed.

The joint mechanism 300 includes an elastic mechanism 330 that is mainly composed of a displacement frame 331, a toggle link 332, and a spring coil 333. The elastic mechanism 330 is a mechanism that exerts, when the sole frame 200 tends to swing beyond the regulated swing range with respect to the lower-thigh frame 101 by a plantar-flexion/dorsiflexion motion performed by the wearer, an elastic force against the swing. Specific actions are described later.

The displacement frame 331 includes a semi-ring-shaped part 331a to which a first-part bushing 334 that receives a shaft surface 320a of the swing shaft 320 and functions as a sliding shaft bearing is fixed, and a plate part 331b in which a part of the toggle link 332 is pivotally disposed. The holder 310 includes an extension part 310a having an external shape similar to the shape of the plate part 331b in a place opposed to the plate part 331b. A part of the toggle link 332 is also pivotally disposed in the extension part 310a. That is, the plate part 331b and the extension part 310a are configured so that they sandwich the toggle link 332 and the spring coil 333 therebetween.

The spring coil 333 is disposed along the z-axis direction which is perpendicular to the swing axis Sa and pivotally connected to the toggle link 332 at both ends thereof. In a situation in which the swing shaft 320 swings within the swing range regulated by the stopper pins 410 and 420, the displacement frame 331 receives an expanding force of the spring coil 333 and thereby is pressed toward the shaft surface 320a (i.e., in the x-axis direction). Note that the installation load of the spring coil 333 is, for example, about 100 N and the pressurization of the displacement frame 331 in the x-axis direction is about 2,000 N.

The holder 310 includes a second-part bushing 314 that receives the shaft surface 320a and functions as a sliding shaft bearing in its semi-cylindrical part that forms a pair with the semi-ring-shaped part 331a of the pressed displacement frame 331. The second-part bushing 314 roughly forms a ring with the first-part bushing 334 and supports the shaft surface 320a of the swing shaft 320 in such a manner that the swing shaft 320 can swing.

It should be noted that the displacement frame 331 is pressed against the holder 310 to prevent the first-part bushing 334 from being pressed against the shaft surface 320a and thereby interfering with the swing of the swing shaft 320 even when the displacement frame 331 is pressed toward the shaft surface 320a. Specifically, the displacement frame 331 has a pressing surface 331c at an end of the semi-ring-shaped part 331a and the press surface 331c presses an opposing receiving surface 310b disposed in the holder 310. By the above-described configuration, since the swing shaft 320 is freely engaged (i.e., engaged with play) in the ring formed by the first-part and second-part bushings 334 and 314, the swing shaft 320 can smoothly swing according to plantar-flexion/dorsiflexion motions performed by the wearer.

Figure 5:
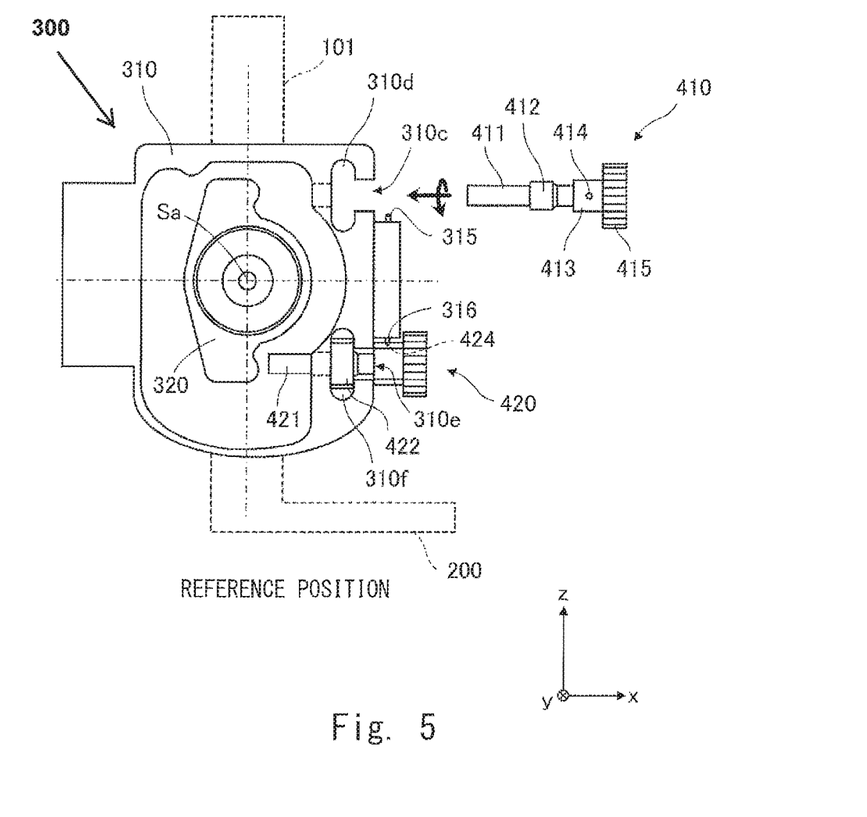
FIG. 5 is a schematic view schematically showing a reference state of the joint mechanism.
Figure 6:
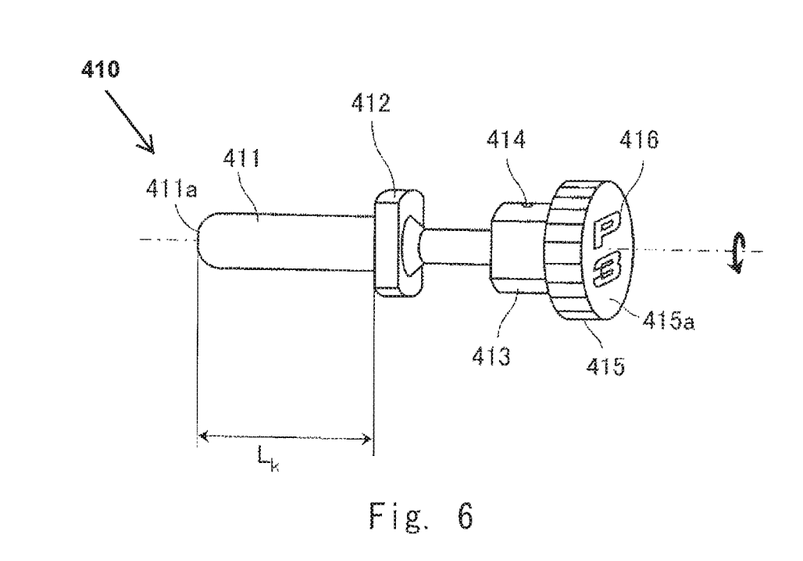
FIG. 6 is a perspective view of an external appearance of a structure of a stopper pin.

FIG. 5 is a schematic view schematically showing a reference state of the joint mechanism 300. Note that the reference state means a state in which the wearer stands upright. In this state, the sole frame 200 is perpendicular to the lower-thigh frame 101. Further, FIG. 6 is a perspective view of an external appearance of a structure of the stopper pin 410.

FIG. 5 shows a state in which the stopper pin 410 for plantar flexion has not been inserted yet. Each of the stopper pin 410 for plantar flexion and the stopper pin 420 for dorsiflexion is replaceable (i.e., removable) for the holder 310. The stopper pin 420 has a structure similar to that of the stopper pin 410 and therefore only the stopper pin 410 is explained.

The stopper pin 410 has a bolt-like shape as a whole, and includes, as viewed from its tip, a projecting pin part 411, a locking part 412, a base-axis part 413, and a knob part 415, all of which are aligned on the central axis. The projecting pin part 411 extends along the central axis in a cylindrical shape and its length is accurately adjusted to a predetermined effective length Lk. Further, a surface of its tip functions as an impact receiving surface 411a that comes into contact with the swing shaft 320.

The locking part 412 has a so-called "two-side cut shape" and the width of the narrowest part is roughly equal to the diameter of the projecting pin part 411. The base-axis part 413 includes a cylindrical part connected to the locking part 412 and a two-side cut shape part connected to the knob part 415. A conical positioning hole 414 is formed on a circular-arc surface of the two-side cut shape part.

The knob part 415 is a part that a user grasps when he/she replaces the stopper pin 410 and is, for example, knurled to improve its grasping property. An inscribed mark 416, which is a mark indicating a property of the stopper pin 410, is formed on a top surface 415a, i.e., an end face of the knob part 415. The inscribed mark 416 is provided so that a user can recognize, at a glance, whether the stopper pin is for plantar-flexion or for dorsiflexion, and/or how long the effective length Lk is (or how large the regulated swing angle is).

An insertion-engagement hole 310c in which the stopper pin 410 for planter-flexion is inserted and an insertion-engagement hole 310e in which the stopper pin 420 for dorsiflexion is inserted are formed on a side surface of the holder 310. Specifically, the insertion-engagement hole 310c is located in a position on a side wall of the holder 310 higher than the swing shaft Sa and penetrates (i.e., extends)

along the x-axis direction to the internal space in which the swing shaft 320 swings. Similarly, the insertion-engagement hole 310e is located in a position on the side wall of the holder 310 lower than the swing shaft Sa and penetrates (i.e., extends) along the x-axis direction to the internal space in which the swing shaft 320 swings.

A locking groove 310d that vertically extends along the z-axis direction is formed at or near the middle of the insertion-engagement hole 310c. Similarly, a locking groove 310f that vertically extends along the z-axis direction is formed at or near the middle of the insertion-engagement hole 310e.

A user inserts the stopper pin 410 for planter-flexion into the insertion-engagement hole 310c. Note that by inserting the stopper pin 410 in such a manner that the narrowest part of the locking part 412 is directed in the vertical direction (i.e., the z-axis direction), the locking part 412 reaches the locking groove 310d. When the user rotates the stopper pin 410 around its central axis by 90 degrees at this point, the locking part 412 is locked in the locking groove 310d. At the same time, a tip of a ball-plunger 315 disposed near the side wall of the holder 310 is engaged in the positioning hole 414 and hence the stopper pin 410 is positioned and fixed to the holder 310.

Similarly, the user inserts the stopper pin 420 for dorsi-flexion into the insertion-engagement hole 310e. Note that by inserting the stopper pin 420 in such a manner that the narrowest part of the locking part 422 is directed in the vertical direction (i.e., the z-axis direction), the locking part 422 reaches the locking groove 310f. When the user rotates the stopper pin 420 around its central axis by 90 degrees at this point, the locking part 422 is locked in the locking groove 310f. At the same time, a tip of a ball-plunger 316 disposed near the side wall of the holder 310 is engaged in the positioning hole 424 and hence the stopper pin 420 is positioned and fixed to the holder 310.

When the stopper pins 410 and 420 are fixed to the holder 310 as described above, their projecting pin parts 411 and 421 project into the internal space in which the swing shaft 320 swings by lengths corresponding to the effective lengths Lk. That is, the projecting pin parts 411 and 421 project in a direction perpendicular to the swing axis Sa of the swing shaft 320. The swing range for planter-flexion motions is regulated according to the projecting length of the projecting pin part 411 and the swing range for dorsiflexion motions is regulated according to the projecting length of the projecting pin part 421.

Figure 7:
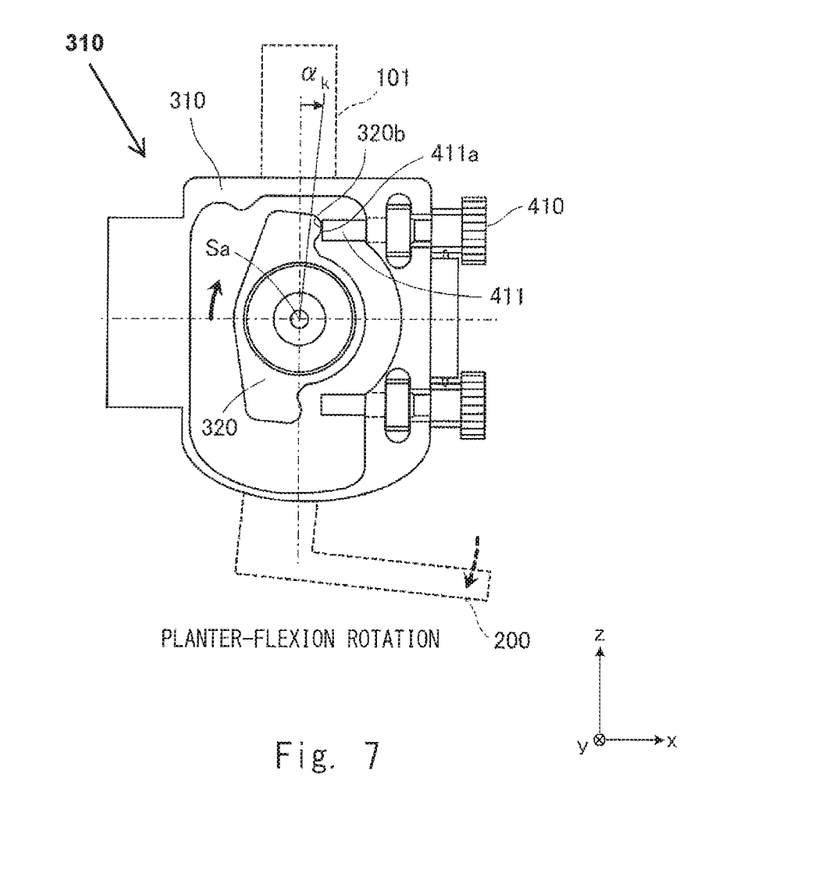
FIG. 7 is a schematic view showing a state of a planter-flexion rotation of a joint mechanism.

FIG. 7 is a schematic view showing a state of a planter-flexion rotation of the joint mechanism 300. The swing shaft 320 includes two arm parts extending in radial directions with respect to the swing axis Sa. An impact surface 320b, which collides with the impact receiving surface 411a, i.e., the surface of the tip of the stopper pin 410, is formed in one of the arm parts. When a wearer performs a planter-flexion motion, the sole frame 200 swings in a direction indicated by a dotted-line arrow in the figure. As a result, the swing shaft 320 swings in a direction indicated by a bold-line arrow. Then, when the swing shaft 320 swings around the swing axis Sa by $\alpha k$ degrees, the impact surface 320b collides with the impact receiving surface 411a. That is, the joint mechanism 300 regulates the swing range so that the swing shaft 320 can swing on the planter-flexion side by $\alpha k$ degrees or smaller.

The stopper pin 410 for planter-flexion is selected by a user from a set of a plurality of stopper pins with projecting pin parts 411 having different effective lengths Lk according to the desired regulated swing range on the planter-flexion side. The impact surface 320b of the swing shaft 320 are processed (e.g., machined) into a cylindrical surface shape so that the impact surface 320b collides with the impact receiving surface 411a of the stopper pin in line contact regardless of which effective length Lk the stopper pin inserted into the insertion-engagement hole 310c has.

Specifically, since the impact receiving surface 411a is a flat surface, the impact surface 320b is processed so that it has a cylindrical surface with respect to the central axis parallel to the swing axis Sa. Since the impact surface 320b collides with the impact receiving surface 411a in line contact regardless of the desired regulated swing angle $\alpha k$, it is possible to disperse an impact force at the time of a collision and thereby to reduce damage and wear of the stopper pin 410. Note that the set of stopper pins may include a stopper pin having an effective length Lk by which the swing angle $\alpha k$ on the planter-flexion side become 0 degrees.

Figure 8:
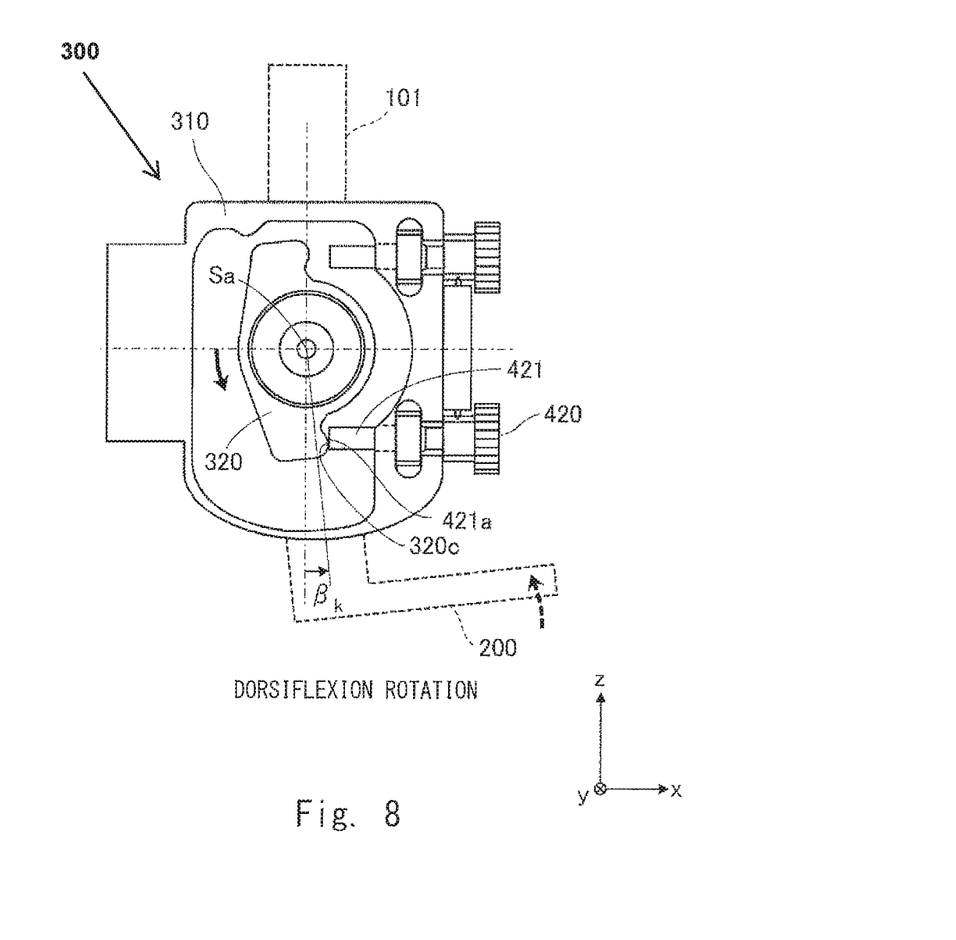
FIG. 8 is a schematic view showing a state of a dorsi-flexion rotation of the joint mechanism.

FIG. 8 is a schematic view showing a state of a dorsi-flexion rotation of the joint mechanism 300. In the swing shaft 320, an impact surface 320c, which collides with an impact receiving surface 421a, i.e., the surface of the tip of the stopper pin 420, is formed in the other of the two arm parts extending in the radial directions with respect to the swing axis Sa, i.e., in one of the two arm parts in which the impact surface 320b is not formed. When a wearer performs a dorsiflexion motion, the sole frame 200 swings in a direction indicated by a dotted-line arrow in the figure. As a result, the swing shaft 320 swings in a direction indicated by a bold-line arrow. Then, when the swing shaft 320 swings around the swing axis Sa by $\beta k$ degrees, the impact surface 320c collides with the impact receiving surface 421a. That is, the joint mechanism 300 regulates the swing range so that the swing shaft 320 can swing on the dorsiflexion side by $\beta k$ degrees or smaller.

Similarly to the stopper pin 410, the stopper pin 420 for dorsiflexion is selected by a user from a set of a plurality of stopper pins with projecting pin parts 421 having different effective lengths Lk according to the desired regulated swing range on the dorsiflexion side. The impact surface 320c of the swing shaft 320 are processed into a cylindrical surface shape so that the impact surface 320c collides with the impact receiving surface 421a of the stopper pin in line contact regardless of which effective length Lk the stopper pin inserted into the insertion-engagement hole 310e has.

Specifically, since the impact receiving surface 421a has a flat surface, the impact surface 320c is processed so that it has a cylindrical surface with respect to the central axis parallel to the swing axis Sa. Since the impact surface 320c collides with the impact receiving surface 421a in line contact regardless of the desired regulated swing angle $\beta k$, it is possible to disperse the impact force at the time of a collision and thereby to reduce damage and wear of the stopper pin 420. Note that a set of stopper pins may include a stopper pin having an effective length Lk by which the swing angle $\beta k$ on the dorsiflexion side become 0 degrees. By selecting the stopper pin 410 by which the swing angle $\alpha k$ on the planter-flexion side become 0 degrees and the stopper pin 420 by which the swing angle $\beta k$ on the dorsiflexion side become 0 degrees, it is possible to fix the joint angle at a reference position.

As has been explained so far, the joint mechanism 300 can regulate the swing angle $\alpha k$ on the planter-flexion side and the swing angle $\beta k$ on the dorsiflexion side in the swing range independently of each other by selecting stopper pins 410 and 420 having appropriate effective lengths Lk and fixing the holder 310 by the selected stopper pins. However, since the regulated swing range is narrower than a range in which a wearer can physically and naturally bend his/her foot as an angle joint function, the impact surfaces 320b and 320c collide with the impact receiving surfaces 411a and 421a, respectively, with large forces. For example, a momentum load of a plantar-flexion/dorsiflexion motion during walking could reach 70 Nm at the maximum. In such a state, an impact force of about 3,500 N is exerted on the impact receiving surface 411a or 421a.

When such an impact force is exerted at every step of walking, the projecting pin parts 411 and 421 are gradually worn out, thus making it impossible to maintain the desired regulated swing angle. In some cases, the projecting pin part 411 or 421 is damaged. As a result, it becomes impossible to accurately manage the allowable range of plantar-flexion/dorsiflexion motions, thus interfering with a rehabilitation plan. Further, frequent replacements of the stopper pins 410 and 420 with new ones are undesirable in view of the cost. Accordingly, the joint mechanism 300 according to this embodiment includes the elastic mechanism 330 to release impacts received on the impact receiving surfaces 411a and 421a and thereby prevents the projecting pin parts 411 and 421 from being worn out or damaged.

Figure 9:
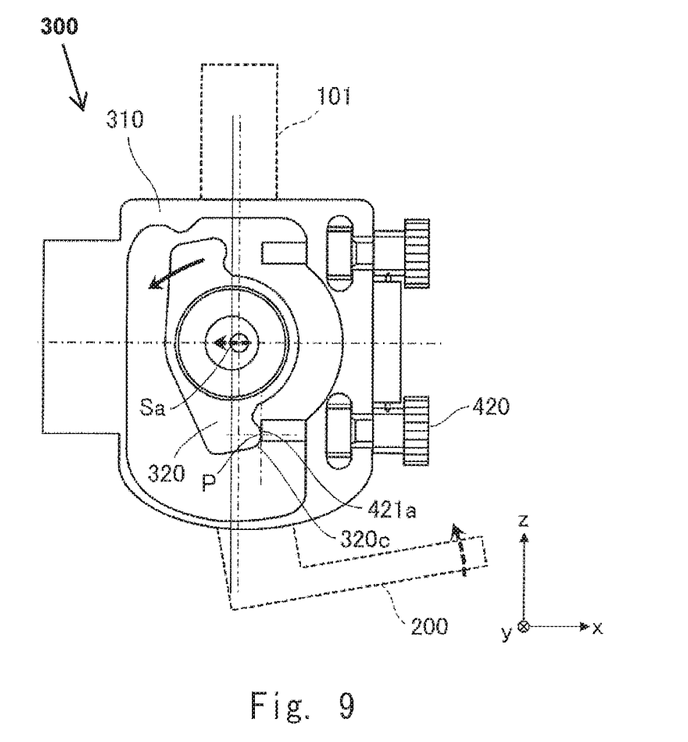
FIG. 9 is a schematic view showing a state in which a swing shaft swings beyond a regulation range.

FIG. 9 is a schematic view showing a state in which the swing shaft 320 swings beyond the regulation range. In this example, a situation in which the sole frame 200 tends to be swung toward the dorsiflexion side beyond the swing angle βk from the state shown in FIG. 8 is assumed.

When the swing angle of the swing shaft 320 reaches the swing angle βk and the sole frame 200 tends to further swing with respect to the lower-thigh frame 101, the swing shaft 320 starts to swing around a contact point P at which the impact surface 320c comes into contact with the impact receiving surface 421a. Specifically, in reality, since the impact surface 320c is in contact with the impact receiving surface 421a in line contact along the y-axis direction as described above, the swing shaft 320 starts to swing around this contact line. In this process, the swing axis Sa shifts from its original position. Note that the swing shaft 320 receives a pressing force in the positive direction on the x-axis from the displacement frame 331 as described later. Therefore, the contact point P gradually moves in the negative direction on the z-axis by the effect of this pressing force and a swinging force that the swing shaft 320 receives from the sole frame 200.

Figure 10:
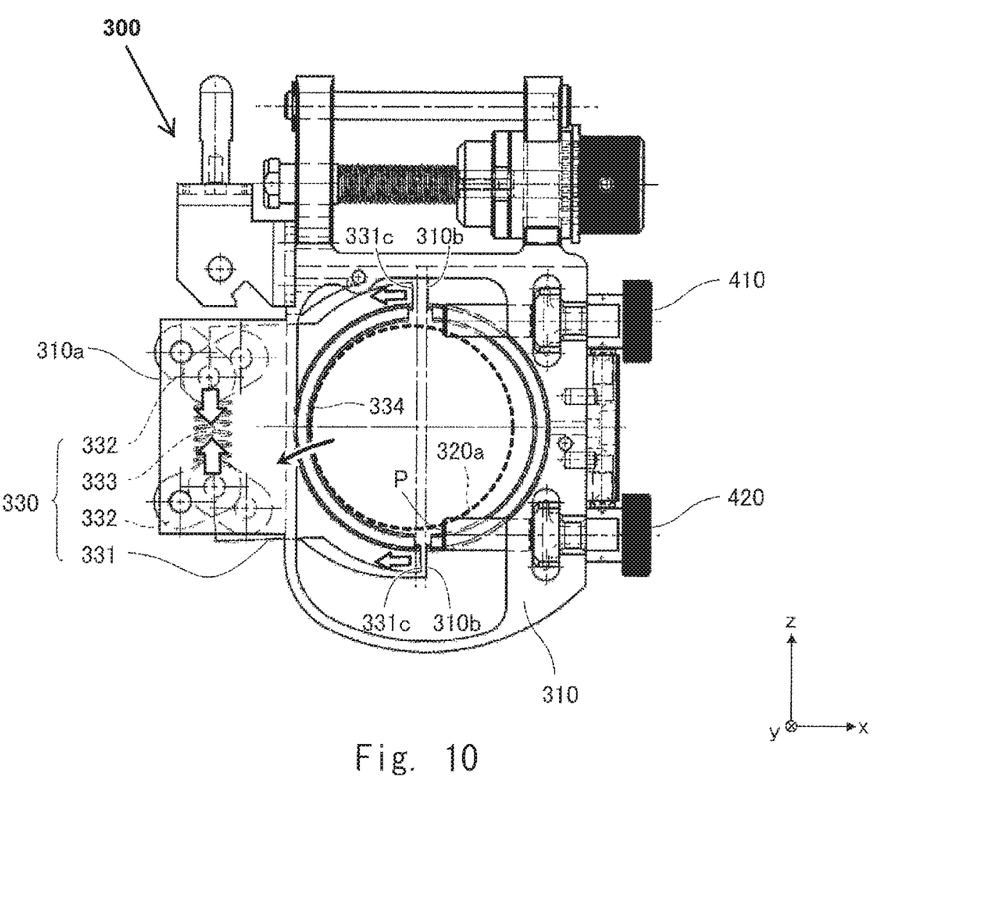
FIG. 10 is a front view showing an action of an elastic mechanism.
Figure 11:
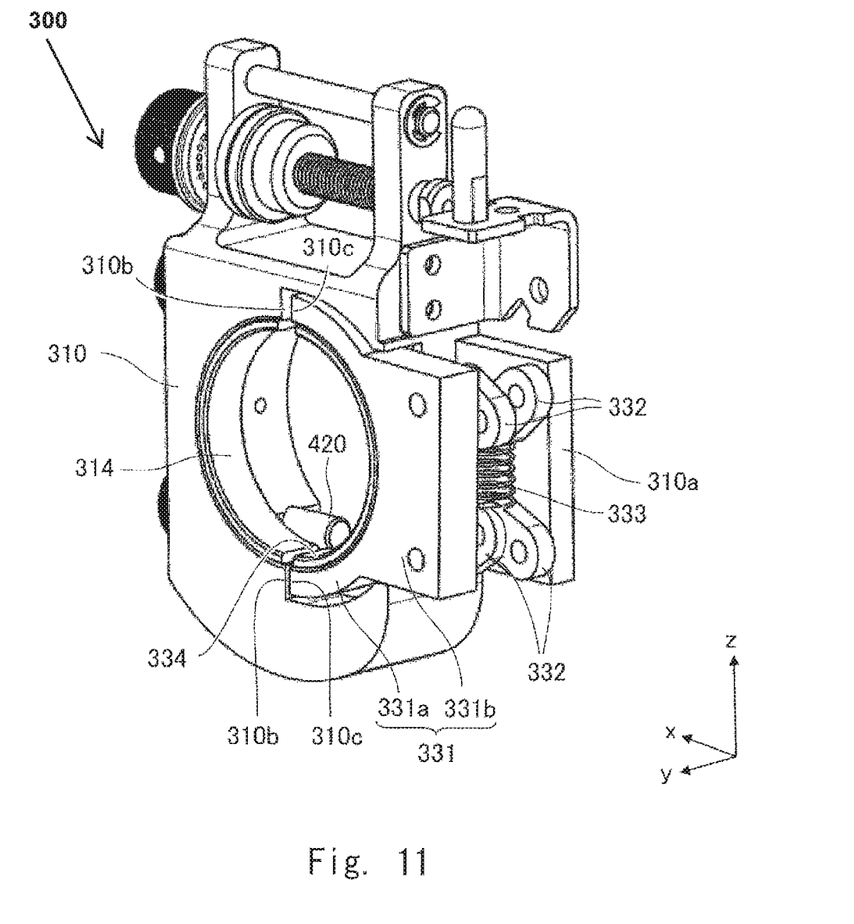
FIG. 11 is a rear-side perspective view showing an action of the elastic mechanism.

FIG. 10 is a front view showing an action of the elastic mechanism 330. Similarly to FIG. 3, a part of the structure that cannot be viewed from the front is indicated by dotted lines. Further, FIG. 11 is a rear-side perspective view showing the action of the elastic mechanism 330. Each of these figures shows a state in which the swing shaft 320 is removed.

When the sole frame 200 tends to further swing beyond the regulated swing range with respect to the lower-thigh frame 101, the elastic mechanism 330 exerts an elastic force against this swing. As described above, after the swing angle of the swing shaft 320 reaches the swing angle βk, a moment around the contact point P acts on the swing shaft 320. At this point, the shaft surface 320a of the swing shaft 320 comes into contact with the first-part bushing 334 and presses the displacement frame 331 through the first-part bushing 334. As a result, the displacement frame 331 starts to be displaced in a direction indicated by a bold-line arrow shown in FIG. 10 by this pressing force and the pressing surface 331c of the displacement frame 331 moves away from the receiving surface 310b of the holder 310. That is, the displacement frame 331 functions as a member that allows the swing shaft 320 to further swing around the contact point P after coming into contact with the stopper pin 420 by displacing the swing axis Sa of the swing shaft 320.

At this point, the spring coil 333 resists the displacement of the displacement frame 331 and thereby indirectly exerts an elastic force against the swing of the swing shaft 320 beyond the regulation range. More specifically, when the displacement frame 331 receives a pressing force from the swing shaft 320 and is thereby displaced, the toggle links 332 pivotally disposed in the plate part 331b of the displacement frame 331 and the toggle links 332 pivotally disposed in the extension part 310a of the holder 310 are turned so that the angles between the links and their counterpart links become smaller, and thereby vertically press the spring coil 333. In this process, the toggle links 332 function as a toggle mechanism and the elastic force of the spring coil 333 sharply increases as the displacement frame 331 starts to be displaced. That is, as a whole, though the elastic mechanism 330 allows the swing shaft 320 to swing slightly beyond the regulation range after the swing shaft 320 reaches the end of the regulation range, the elastic mechanism 330 releases the impact force exerted on the stopper pin 410 or 420.

Note that as described above, the spring constant of the spring coil 333 is adjusted so that the pressurization of the displacement frame 331 in the x-axis direction becomes about 2,000 N. Therefore, in a situation in which the swing shaft 320 swings within the swing range regulated by the stopper pins 410 and 420, the displacement frame 331 is not displaced. In other words, the swing axis Sa of the swing shaft 320 is not displaced as long as the swing shaft 320 swings within the regulated range.

Further, as described above, the spring coil 333 is disposed along the z-axis direction. By disposing the spring coil 333 along the circumferential direction with respect to the swing axis Sa, the sizes of the plate part 331b of the displacement frame 331 and the extension part 310a of the holder 310 can be reduced. Eventually, it is possible to reduce the space necessary for the joint mechanism 300.

Figure 12:
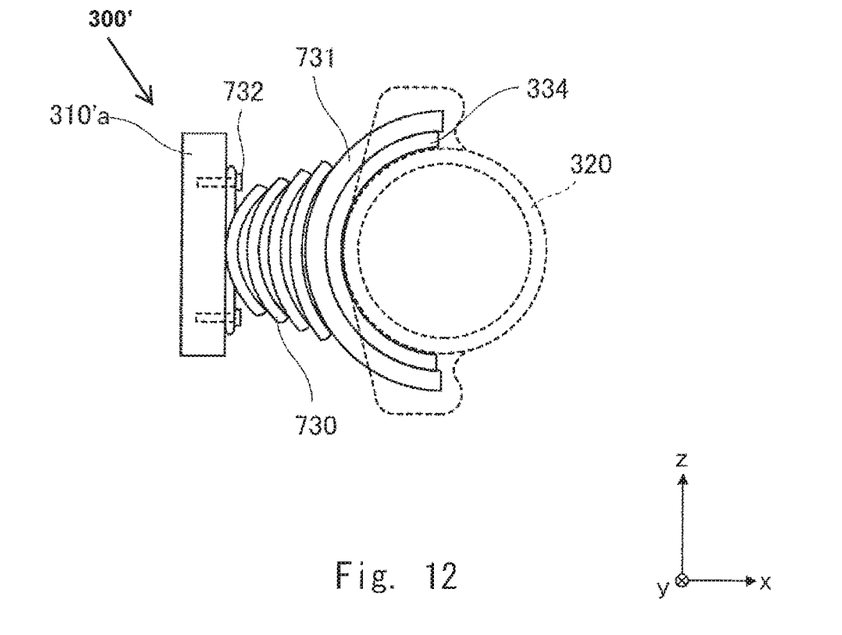
FIG. 12 is a schematic view schematically showing a structure of another example of a joint mechanism.

Next, modified examples of the above-explained joint mechanism 300 are explained. FIG. 12 is a schematic view schematically showing a structure of a part of a joint mechanism 300', which is another example of the joint mechanism 300. Note that structures similar to those of the above-described joint mechanism 300 are omitted except for the structure that is specifically explained below.

The joint mechanism 300' differs from the joint mechanism 300 because the joint mechanism 300' uses a laminated spring 730 instead of using the spring coil. A displacement frame 731 has a circular-arc shape for supporting the first-part bushing 334 inside thereof and fixes one side of the laminated spring 730 on the outer side of the circular-arc. The other side of the laminated spring 730 is fixed to an extension part 310'a of the holder 310 by screws 732.

Even in the joint mechanism 300' having the above-described structure, it is possible, when the sole frame 200 tends to swing beyond the regulated swing range with respect to the lower-thigh frame 101 by a plantar-flexion/dorsiflexion motion performed by a wearer, to exert an elastic force against the swing as in the case of the above-described joint mechanism 300.

Figure 13:
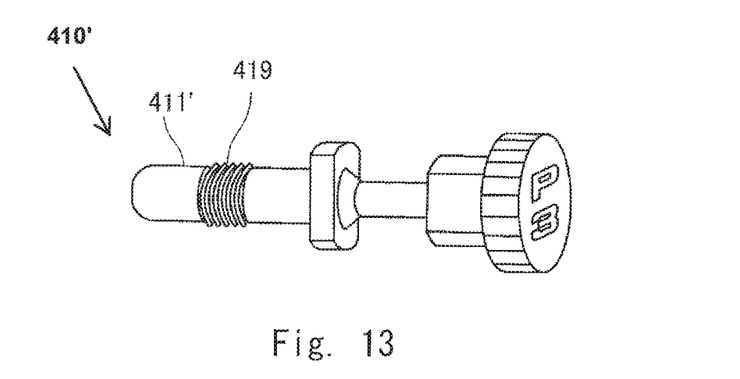
FIG. 13 is a perspective view of an external appearance showing a structure of another example of stopper pin.

FIG. 13 is a perspective view of an external appearance showing a structure of a stopper pin 410', which is another example of the stopper pin 410. The stopper pin 410' differs from the stopper pin 410 because the stopper pin 410' includes a shock-absorbing spring 419 in the middle of a projecting pin part 411'. The shock-absorbing spring 419 functions as an elastic member that releases an impact that the projecting pin part 411' receives from the swing shaft 320. By using such a stopper pin for each of the planter-flexion side and the dorsiflexion side, the need for the above-described mechanism such as the displacement frame 331, the toggle link 332, and the like can be eliminated.

In the above-explained ankle joint regulating apparatus, the holder 310 is described as a component of the joint mechanism 300. However, the structure of the holder 310 may be incorporated into the lower-thigh frame 101. Further, the regulation member that regulates the swing range is not limited to the form of a stopper pin. The regulation member may be a block-like member instead of a pin-like member. The regulation member may be a two-forked structure that serves for both the planter-flexion and the dorsiflexion. Further, although the regulation member that regulates the swing range of the swing shaft 320 is preferably replaceable (i.e., removable) in view of the usability, it does not necessarily have to be replaceable. For example, in the case in which a plurality of ankle joint regulating apparatuses having different regulated ranges are prepared, the regulation member may be integrally formed with the holder 310 and/or the lower-thigh frame 101.

In the above-explained embodiments, an ankle joint regulating apparatus attached to an ankle joint, in which relatively large impacts occur in both ends of the regulated swing range, is explained. However, use of the above-described joint mechanism is not limited to use for ankle joint regulating apparatuses. That is, the above-described joint mechanism can be used for joint regulating apparatuses used for any kinds of joints, provided that the joint mechanism supports a first member attached to a part of a body located on a side of one of bones and a second member attached to a part of the body located on a side of the other bone so that they can swing in a regulated swing range. An ankle joint regulating apparatuses including such a joint mechanism does not require electric control and have a simple structure and high durability.

From the invention thus described, it will be obvious that the embodiments of the invention may be varied in many ways. Such variations are not to be regarded as a departure from the spirit and scope of the invention, and all such modifications as would be obvious to one skilled in the art are intended for inclusion within the scope of the following claims.

What is claimed is:

1. A joint regulating apparatus configured to regulate a movable range of a joint connecting a first bone part of a wearer with a second bone part of the wearer, comprising:
   a first member configured to be attached to a part of a body located on a side of the first bone part;
   a second member configured to be attached to a part of the body located on a side of the second bone part; and
   a joint mechanism configured to support the first and second members so that the first and second members can swing with respect to each other along a movable direction of the joint in a predetermined regulated swing range, the joint mechanism including an elastic mechanism,
   wherein the elastic mechanism is configured to exert an elastic force against the swing to restrict the first and second members from swinging with respect to each other beyond the swing range, and the elastic mechanism is configured to not exert an elastic force against the swing, when the first and second members swing with respect to each other within the swing range,
   wherein the joint mechanism comprises:
      a regulation member directly or indirectly fixed to the first member, the regulation member being configured to regulate the swing range; and
      a swing member directly or indirectly fixed to the second member, the swing member being configured to come into contact with the regulation member at one of the ends of the swing range and at the other end of the swing range, and
   the elastic mechanism comprises:
      a displacement member configured to allow the swing member, after the swing member comes into contact with the regulation member, to further swing around a contact point by displacing a swing axis of the swing member: and
      an elastic member configured to exert an elastic force by resisting a displacement of the displacement member.

2. The joint regulating apparatus according to claim 1, wherein the elastic member presses the displacement member so that the swing axis is not displaced when the swing member swings within the swing range.

3. The joint regulating apparatus according to claim 2, wherein the joint mechanism comprises:
   a first-part bushing integrally formed with a holder part, the holder part being configured to support the regulation member, the first-part bushing being configured to receive a shaft surface of the swing member; and
   a second-part bushing integrally formed with the displacement member, the second-part bushing being configured to form a ring with the first-part bushing and thereby to receive the shaft surface.

4. The joint regulating apparatus according to claim 3, wherein the displacement member has a contact surface configured to receive a pressing force from the elastic member and thereby to come into contact with the holder part when the swing member swings in the swing range, and
   the second-part bushing is not pressed onto the shaft surface by the elastic member.

5. The joint regulating apparatus according to claim 1, wherein
   the elastic member is a spring, and
   the displacement member is connected to the spring though a toggle mechanism.

6. The joint regulating apparatus according to claim 5, wherein the spring is a spring coil disposed along a circumferential direction with respect to the swing axis.

7. The joint regulating apparatus according to claim 1, wherein
   one of the first and second members is a lower-thigh frame configured to be attached to a lower thigh of the wearer,
   the other of the first and second members is a sole frame on which the sole of the wearer is configured to be placed, and
   in the joint mechanism, the swing range is determined so that a range of a plantar-flexion motion and a dorsi-flexion motion of an ankle joint of the wearer is configured to be regulated during use.

* * * * *